(12) United States Patent
Asotra et al.

(10) Patent No.: US 7,758,877 B2
(45) Date of Patent: Jul. 20, 2010

(54) STABLE LORATADINE SPILL RESISTANT FORMULATION

(75) Inventors: Satish Asotra, Brampton (CA); Shen Gao, Brampton (CA); Xiaoli Wang, Mississauga (CA)

(73) Assignee: Taro Pharmaceuticals U.S.A., Inc., Hawthorne, NY (US)

( * ) Notice: Subject to any disclaimer, the term of this patent is extended or adjusted under 35 U.S.C. 154(b) by 0 days.

(21) Appl. No.: 11/049,310

(22) Filed: Feb. 2, 2005

(65) Prior Publication Data

US 2005/0175642 A1 Aug. 11, 2005

Related U.S. Application Data

(60) Provisional application No. 60/542,056, filed on Feb. 5, 2004.

(51) Int. Cl.
*A61K 31/55* (2006.01)
*A61K 31/473* (2006.01)
*A61K 9/00* (2006.01)

(52) U.S. Cl. .................. 424/400; 514/217.05; 514/290

(58) Field of Classification Search .................. 424/400
See application file for complete search history.

(56) References Cited

U.S. PATENT DOCUMENTS

| | | | | |
|---|---|---|---|---|
| 2,921,884 | A * | 1/1960 | Nachod et al. | 424/9.455 |
| 5,006,360 | A * | 4/1991 | Howard et al. | 426/601 |
| 5,384,134 | A * | 1/1995 | Kross et al. | 424/661 |
| 5,384,311 | A * | 1/1995 | Antenucci et al. | 514/53 |
| 5,881,926 | A | 3/1999 | Ross et al. | |
| 6,051,585 | A * | 4/2000 | Weinstein et al. | 514/335 |
| 6,071,523 | A * | 6/2000 | Mehta et al. | 424/400 |
| 6,102,254 | A * | 8/2000 | Ross | 222/192 |
| 6,132,758 | A | 10/2000 | Munayyer et al. | |
| 6,355,258 | B1 | 3/2002 | Mehta et al. | |
| 6,399,079 | B1 | 6/2002 | Mehta et al. | |
| 6,557,732 | B2 * | 5/2003 | Van Rompuy et al. | 222/136 |
| 6,656,482 | B2 | 12/2003 | Mehta et al. | |
| 6,745,919 | B2 | 6/2004 | Moros et al. | |
| 2003/0049633 | A1 * | 3/2003 | Ashkenazi et al. | 435/6 |
| 2003/0235618 | A1 | 12/2003 | Moros et al. | |
| 2004/0101563 | A1 | 5/2004 | Kundu et al. | |
| 2004/0258716 | A1 | 12/2004 | Gao et al. | |

OTHER PUBLICATIONS

Taylor. Archimedes, a gold thief and buoyancy. Sources. Jul./Aug. 1993; p. 27-30.*
Wikipedia (http://en.wikipedia.org/wiki/Buoyancy).*
International Search Report dated Nov. 24, 2005, issued in PCT/US2005/002660.
U.S. FDA Center for Drug Evaluation and Research, Approval Package for Appl. No. 20-641/SE5-007, Final Printed Labeling (1999).

* cited by examiner

*Primary Examiner*—Jake M. Vu
(74) *Attorney, Agent, or Firm*—Venable LLP; Michael A. Gollin; Thomas F. Barry

(57) ABSTRACT

The present invention provides for a storage stable pharmaceutical liquid suspension for oral administration having a pharmaceutically effective amount of an antihistamine. The storage stable suspension preferably contains loratadine. The present invention further provides a process of preparing the storage stable pharmaceutical liquid suspension as well as a method of treating a mammal with a therapeutically effective amount of loratadine in the stable pharmaceutical liquid suspension.

12 Claims, No Drawings

STABLE LORATADINE SPILL RESISTANT FORMULATION

BACKGROUND OF THE INVENTION

Loratadine is a long acting, non-sedating antihistamine with no significant sedative or anti-muscarinic activity. Loratadine is virtually completely water insoluble under neutral pH. Loratadine solutions having a pH of between 2.5 to 3.1 are disclosed in U.S. Pat. No. 6,132,758. A major disadvantage of loratadine in an aqueous solution is the oxidative degradation of the compound into inactive metabolites. U.S. Pat. No. 6,132,758 describes stable loratadine syrups that include aminopolycarboxylic acids and salts thereof as antioxidants to prevent the oxidative degradation.

Syrups, elixirs, solutions, and suspensions are traditional dosage forms for oral medication. These liquid formulations are typically measured by pouring into a spoon, but this approach has the great drawback of spillage. The risk of spillage can cause people to underfill or spill from the spoon, leading to inaccurate dosage. With elderly people, children, and the infirm, lack of motor skills or poor attention can cause difficulty in filling a spoon with a liquid and bringing it to the mouth and can be a serious impediment to administering the medicine. Solid formulations such as pills, tablets, and capsules are also difficult for children and for elderly, infirm people to swallow Recently, spill resistant pharmaceutical preparations for the oral delivery of pharmaceutically active agents have been described in the commonly owned U.S. Pat. Nos. 5,881,926, 6,071,523, 6,102,254, 6,355,258, and 6,399,079, herein incorporated by reference. These patents describe oral dosage forms for the delivery of active agents that do not spill easily, are organoleptically pleasing and are storage stable.

Surprisingly, we have found that loratadine in a spill resistant pharmaceutical suspension is resistant to oxidative degradation and has increased rheological storage stability as compared to solutions of loratadine.

SUMMARY OF THE INVENTION

The invention relates to a rheological and storage stable semi-solid pharmaceutical suspension for oral administration of antihistamines, comprising a suspension of an effective amount of water insoluble active ingredient in a pharmaceutically acceptable aqueous suspension-stabilizing vehicle.

The invention relates to a palatable stable oral suspension of loratadine or a chemically related antihistamine, including any pharmaceutically acceptable salt thereof. This formulation is homogenous and does not degrade by oxidation or esterfication into non-active ingredients.

The invention relates to a pharmaceutical suspension comprising about 0.01% up to about 0.10% of an antihistamine (w/w), from about 29 to about 64% water (w/w), up to about 50% glycerin (w/w), up to about 20% sorbitol (w/w), up to about 10% propylene glycol (w/w) and up to about 0.50% of a thickening agent (w/w).

The invention relates to a stable pharmaceutical suspension comprising about 0.088% loratadine (w/w), about 0.24% to 0.32% (w/w) Carbomer 934P, about 0.01% (w/w) sodium hydroxide, about 0.10% (w/w) Poloxamer 188, about 5.0% (w/w) propylene glycol, about 50.0% (w/w) glycerin, about 5.0% (w/w) sorbitol (crystalline), about 0.20% (w/w) sucralose liquid concentrate, about 0.018% butylparaben, about 0.30% (w/w) masking agent, about 0.10% peach flavor, and about 38.9% purified water.

The invention relates a stable pharmaceutical suspension, wherein Loratadine at a concentration of about 0.088% (w/w) is suspended in a uniformly dispersed manner in an aqueous suspension without agitation during the product shelf-life and wherein the pharmaceutical suspension has the following properties:
  antimicrobial activity;
  no oxidation of the loratadine;
  a viscosity of between about 5,000 cps to about 15,000 cps;
  a product shelf-life of up to about six months;
  no crystalline growth during a heat-cool study for three days at about 45° C.; Bingham behavior of the pharmaceutical suspension may have a yield value of from about 0.3 to about 200 D/cm$^2$; and an acceptable palatability.

The pharmaceutical suspension may comprise at least one additional component selected from the group consisting of excipients, surface active agents, dispersing agents, inert diluents, granulating agents, disintegrating agents, binding agents, lubricating agents, sweetening agents, flavoring agents, coloring agents, preservatives, oily vehicles, solvents, suspending agents, dispersing agents, wetting agents, emulsifying agents, demulcents, buffers, salts, fillers, antibiotics, antifungal agents and stabilizing agents.

The invention provides a pharmaceutical suspension for oral administration, comprising a suspension of an effective amount of particles of an antihistamine in a pharmaceutically acceptable aqueous suspension-stabilizing vehicle, the suspension having the following qualities:
  a homogeneity wherein the antihistamine is uniformly dispersed but not dissolved in the vehicle;
  a crystalline stability such that the active ingredient particles stay within a target particle size range during heat-cool studies;
  a suspension stability such that the active ingredient remains suspended during the product shelf-life without agitation;
  a Brookfield viscosity within the range of about 6,000 cps to about 20,000 cps at room temperature;
  an antimicrobial activity;
  no oxidation of the loratadine; and
  an acceptable palatability.

The antihistamine particles may be crystals that neither dissolve nor grow substantially when the sample is heated to about 45° C. and cooled to room temperature repeatedly. The vehicle may have a density about equal to that of the active ingredient.

In suspensions of the invention, the composition can be squeezed into a spoon from a container with light manual pressure, to spread and level in a spoon bowl quickly enough for accurate measurement and to remain in the spoon bowl long enough to permit administration without spilling. In inventive suspensions, the composition spreads and levels in a spoon bowl within about 1-5 seconds at room temperature, and remains in the spoon bowl for at least about 30 seconds on spoon inversion, about 30 seconds on spoon vibration, and about 1 second on spoon tilting. In exemplary formulations, the composition:
  (a) is non-Newtonian and a time independent fluid;
  (b) is pseudoplastic, and
  (c) exhibits Bingham behavior.

The compositions may have a yield value of between about 0.3 to about 200 D/cm$^2$.

Inventive pharmaceutical suspensions for oral administration comprise a suspension of (a) an effective amount of particles of an antihistamine that are insoluble in the vehicle, have a predetermined particle size range, and a desired dissolution profile after ingestion; and (b) a fluid vehicle that is pharmaceutically acceptable, aqueous, and suspension-stabilizing, comprising a thickener component, a crystal conditioning surfactant, a carrier component, and organoleptic components, the vehicle having a specific gravity about the same as that of the particles of the active ingredient.

The suspensions may comprise a carbomer, such as carbomer 934P at a concentration in the range from about 0.40 to about 0.48%, w/w. The carbomer 934P may be neutralized to a pH range of about 6.4 to about 7.3.

The surfactant may be a poloxamer, and may be in a concentration in the range of from about 0.02% to about 0.5%, w/w. The carrier component may comprise propylene glycol and/or glycerin, for example propylene glycol in a range of from about 5% to about 20.0%, w/w and/or glycerin in a range of from about 33% to about 39.0%, w/w. The suspension may comprise sucralose liquid concentrate, aspartame, saccharin and/or sorbitol crystalline.

The invention provides for a method of preparing a formulation for oral delivery of an antihistamine in a storage and Theologically stable spill resistant pharmaceutical suspension that is organleptically pleasing.

DETAILED DESCRIPTION

In describing embodiments of the present invention, specific terminology is employed for the sake of clarity. However, the invention is not intended to be limited to the specific terminology so selected. It is to be understood that each specific element includes all technical equivalents, which operate in a similar manner to accomplish a similar purpose. The above-described embodiments of the invention may be modified or varied, and elements added or omitted, without departing from the invention, as appreciated by those skilled in the art in light of the above teachings. Each reference cited herein is incorporated by reference as if each were individually incorporated by reference.

The inventive suspension is an antihistamine evenly dispersed in a semi solid aqueous vehicle. The semi-solid formulation of the invention can be described as follow. The suspension has a homogenity that is uniformly dispersed but undissolved in the vehicle. The formulation consists of mutually compatible components at room temperature, and being a spill resistant semi solid. It may have a crystalline stability such that the antihistamine does not exhibit excessive crystalline growth or dissolution, and the particles stay within a target particle size range. Heat-cool studies can be conducted to check for crystal growth.

The inventive suspension comprises a vehicle that is pharmaceutically acceptable, aqueous, and suspension-stabilizing, comprising a thickener component and a carrier component, and may include organoleptic components. The suspension provides a method of treating allergic conditions in mammals. The methods include administering to a subject suffering from an allergic condition a storage stable pharmaceutical composition according to the invention. In one embodiment, the subject is a human. In another embodiment the allergic condition is seasonal allergic rhinitis or chronic idiopathic utirmcaria. The storage stable pharmaceutical composition can be administered to a patient in a dosage range of, for example, 0.5 mg to about 15 mg per day, preferably about 1 mg to about 12 mg per day, and more preferably 5 to 10 mg per day.

The thickener provides the necessary viscosity, spill-resistant properties such as pseudoplasticity, to suspend the active agent. Carbomers (Merck Index $12^{th}$ ed., no. 1878) can be used as thickeners in semisolid pharmaceutical formulations (see Mehta et al., U.S. Pat. No. 6,071,523). Carbomer 934P (Carbopol® 974P) is a suitable thickener or gelling agent. Suitable concentrations from about 0.2 to about 1.0%, and more specifically from about 0.22 to about 0.28%, w/w. Its rheology supports a high yield value (Handbook of Pharmaceutical Excipients Third Ed., A. H. Kibbe (Ed.), Pharmaceutical Press, London, UK., 2000, Pg. 442, 79, 53 ("Handbook of Pharm. Excipients")). Carbomers are slightly acidic and must be neutralized e.g. with sodium hydroxide (as needed to neutralize the carbomer up to about 0.08% in particular formulations) with a preferred pH range being about 6.4 to about 7.3, providing the maximum viscosity plateau.

The carrier component serves as the external phase of the suspension. The carrier component comprises propylene glycol up to about 20% or from about 3 to about 10%. The carrier may also comprise glycerin up to about 50%. Purified water comprises the bulk of the carrier component comprising from about 29% to about 64% of the formulation.

The suspension has antimicrobial activity. Propylparaben (up to about 0.04%) and butylparaben (0.018% to about 0.18%) are suitable. Other antimicrobial excipients may also be used. These suspensions are alcohol-free.

The organoleptic ingredients improve the taste and appearance and do not negatively affect the suspension stability. The organoleptic agents in the following examples include coloring and flavoring agents, sweeteners and masking agents.

The formulation requires a crystal conditioning surfactant, i.e., a wetting agent, that prevents the antihistamine from aggregating. The extreme hydrophobic properties of loratadine necessitate a wetting agent to disperse the antihistamine in the formulation. A concentration of from about 0.05% to about 0.5% poloxarner 188 was found to be the most effective at wetting the loratadine without the formation of excessive foaming.

The antihistamine spill resistant suspensions are non-Newtonian and time independent fluids. Non-Newtonian refers to a fluid whose behavior departs from that of an ideal Newtonian fluid. These fluids have different viscosities at different shear rates and fall under two groups: time independent and time dependent. In contrast, for a Newtonian fluid the rate of shear in the fluid under isothermal conditions is proportional to the corresponding stress at the point under consideration. Time independent fluids are those for which the rate of shear at any point in the fluid is some function of the shear stress at that point and depends on nothing else. These fluids have a constant viscosity value at a given shear rate. The viscosities do not change with time. (McGraw-Hill Encyclopedia of Science & Technology, $6^{th}$ edition, 1987, Volume 12, pages 57-60).

Spill resistant semi-solid formulations are formulations that have a viscometric yield value determined as a relative value, e.g. using a Brookfield Viscometer to measure a shear vs. stress curve. Ease of administration is intended to mean (a) extrudability under light manual pressure from a squeezable container or a proxy (e.g. a syringe with a 5 mm orifice), and (b) spreadability in a spoon bowl measured by extruding the formulation into a spoon bowl and determining whether the material levels or spreads to the edges of the spoon bowl. Spreadability also contributes to accuracy of measurement.

A spill-resistant formulation according to the invention begins to spill from a spoon bowl during test periods of vibrations, inversion, and tilting, but slowly enough to conform with practical time limits between dispensing and ingesting, and quickly enough to enable the product to be readily consumed from a spoon bowl by a patient. In particular, spill resistance means the formulation does not spill from a teaspoon for a definite period, e.g. at least 30 to 60 seconds on spoon inversion, about 30 to 60 seconds on spoon vibration and about 10, 20, to 30 seconds on spoon tilting. The shaking, tilting and inversion tests are performed on an experimental platform as described in U.S Pat. No. 6,071,523. The tests ensure that dispensing and dosing to a 5.0 mL spoon is easy and accurate.

The rheogram of these suspensions may be pseudoplastic. The viscosity of the gel decreases with increasing shear rate, and the behavior is fully reversible. A pseudoplastic fluid's ratio of shear stress to the rate of shear, which may be termed the apparent viscosity, falls progressively with shear rate. The decrease in viscosity with an increase in shear rate is also known as shear thinning. This phenomenon of shear thinning is characteristic of suspensions of asymmetric particles or solution of polymers such as cellulose derivatives. The viscosity of spill resistant gel decreases with increasing the shear rate, e.g., increasing the spindle speed. The suspensions of the inventive formulation are not thixotropic.

The viscosity of the composition of the invention can be varied by the choice and amount of thickening agent and other components to a consistency which permits the composition to be readily squeezed and flow through a relatively narrow orifice, i.e. of the order of about 1 to 10 mm in diameter.

The term "spill resistant formulation" refers here to a product which, as sold, has viscosity in a certain range (e.g. 5,000 to 20,000 cps), is a semi-solid, is easy to administer accurately, has spill-resistant consistency, is storage stable, and has mutually compatible ingredients, as described in Mehta et al., U.S. Pat. No. 6,071,523. Viscosity can be measured using a Brookfield Viscometer with a 'T-C' spindle at 20 RPM and 20-25 degrees C., or equivalent. Viscosity decreases slightly with increasing temperature.

The pharmaceutical compositions of the invention comprise a pharmaceutical agent in an effective amount for systemic treatment by oral administration in admixture with a pharmaceutically acceptable vehicle comprising a thickening agent in a amount which provides a semisolid, such as a gel or a paste suspension. The semisolid has a Brookfield viscosity in a range of at least about 5,000, 6,000, 7,000, or 8,000 cps, and less than about 11,000, 12,000, 13,000 or 15,000. Thus, desirable ranges include about 5,000-15,000 cps, 5,000-20,000 cps, 6,000-17,000, or about 8,000 to about 11,000 cps.

The spill resistant pharmaceutical formulation of the present invention may also contain additional active pharmaceutical ingredients, such as for example, decongestants, analgesics, antitussives and expectorants. Any specific drug within these therapeutic classes is suitable for inclusion in the present invention. Illustrative examples include analgesics such as aspirin, acetaminophen, naproxen, ketoprofen and ibuprofen; decongestants such as pseudoephedrine or phenylpropanolamine; antitussives such as codeine, hydrocodone, or dextromethorphan; and expectorants such as guaifenesin, including salts thereof.

A benefit of the spill resistant formulation over the previously described loratadine formulations is that the ingredient remains suspended indefinitely without agitation, that is without stirring or shaking. This is an improvement over known formulations, as the dispensed dose is always uniform over the shelf life of the product. The formulation of the invention can not be shaken easily, so the particles must remain suspended without shaking.

Mutual compatibility of the components means that they do not separate in preparation and storage for the equivalent of two years at room temperature (as indicated by three months accelerated stability testing at 40° centigrade and 75% relative humidity). Storage stability means that the materials do not lose their desirable properties during storage for the same period. Preferred compositions do not exhibit a drop in viscosity of more than 50% or an increase in viscosity of more than 100% during that period.

Another benefit of the presently described formulation over the previously described formulations is that the loratadine spill resistant formulation does not oxidize to active or inactive metabolites. The inventive formulations are storage stability may in that the active pharmaceutical agent of the composition, the antihistamine, is not oxidized to it's active or inactive metabolites. Degradation of syrup formulations containing loratadine or related antihistamines was observed during storage stability testing, as evidenced by declining concentrations of the active ingredient and a concomitant formation of impurities. Two of the impurities which form in loratadine syrups have been identified as 2-Hydroxymethyl loratadine ("2-HML") and 4-Hydroxymethyl loratadine ("4-HML"), while other unidentified impurities occur regularly and have been collectively denoted as "Group A"; these materials number about 5 to 7 and elute together in an HPLC analysis, at retention times which indicate a higher polarity than that of loratadine. An analysis of the inventive suspension reveals that the product is stable to oxidative degradation, and no impurities are seen when tested over the shelf life of the product.

EXAMPLES

Example 1

The Loratadine spill resistant suspension was formulated to contain the following ingredients:

TABLE I

| INGREDIENTS | % (w/w) |
| --- | --- |
| Loratadine | 0.088% |
| Purified Water | 38.9 |
| Glycerin | 50 |
| Sorbitol (Crystalline) | 5.0 |
| Propylene Glycol | 5.0 |
| Carbomer 934P (Carbopol ® 974P) | 0.24%-0.32% |
| Poloxamer 188 | 0.10% |
| Sodium Hydroxide | 0.01% |
| Sucralose Liquid Concentrate | 0.20 |
| Butylparaben | 0.018% |
| Masking Agent | 0.30 |
| Peach flavor | 0.10 |

Example 2

Process for Preparing a Spill Resistant Loratadine Suspension

The Loratadine spill resistant suspension was prepared in the following manner:

Step 1: Butylparaben (0.18 grams) was dissolved in 50 grams of propylene glycol. 20 grams purified water and 1.0 gram Poloxamer 188 were mixed in a stainless steel pot until a clear solution is formed and then added to the propylene glycol mixture.

Step 2: 120 grams of glycerin was placed in a stainless steel pot and the Poloxamer solution of step I was added. A Caframo mixer (Ontario, Canada), was used to mix for approximately 5 minutes until a clear solution was formed. The stirrer was adjusted to yield a vortex in the stainless steel pot. 0.880 grams of loratadine was slowly added to the center of the vortex. 1 gram of Peach Flavor and 3 grams of masking agent were then added. 20 grams of glycerin was used to rinse. The ingredients were then mixed until a smooth slurry was formed.

Step 3: In another stainless steel pot 294.6 grams of purified water and 3.0 grams of sucralose concentrate were added. 3.2 grams of Carbomer 934 P (Carbapol® 974P) was then slowly added. The solution was mixed with a Caframo mixer until a smooth solution was formed. 50 grams of sorbital crystalline was added until completely dissolved. 380 grams of Glycerin was added and mixed at 300±200 rpm for 10 minutes. 5.94 grams of purified water and 0.66 grams of sodium hydroxide were added and mixed for approximately 10 minutes to a final pH of 6.4 to 7.3.

Step 4: The loratadine phase was added to the stainless steel pot and mixing continued for approximately 30 minutes.

Example 3

The following HPLC method was developed to measure 2-hydroxymethyl loratadine and 4-hydroxymethyl loratadine in the spill resistant suspension.
Mobile Phase Preparation
  Mobile Phase Buffer Solution (pH2.5) 3.8 g of hexane sulphonate sodium salt and 5.3 g of ammonium sulfate were dissolved in 200 mL of water. The solution was mixed well. The pH was adjusted to 2.50±0.05 with o-phosphoric acid (85%).
  Mobile Phase A (30:70 ACN:Buffer) 300 mL of aceonitrile was combined with 700 mL of the buffer solution and mix. The mixture was filtered through a 0.45 µm membrane filter and degassed.
  Mobile Phase B (100% CAN) Acetonitrile was filtered through a 0.45 µm membrane filter and degassed.
  Sample Solvent (80:20 Methanol:Buffer
  Sample Buffer Solution (pH 2.1) 1.9 g of 1-hexane sulphonate sodium and 2.7 g of ammonium sulfate were dissolved in 1000 mL of water and mixed well. The pH was adjusted to 2.10±0.05 with o-phosphoric acid (85%).
  Sample Solvent (80:20 MeOH:Buffer) 800 mL of methanol was added to 200 mL of the buffer solution and mixed well.
HPLC Set-up
  Column: Symmetry C18, 4.6 mm×250 mm, 5 µm particle size
  Temperature: 30° C.
  Flow Rate: 1.2 mL/min
  Injection Vol.: 20 µl
  Wavelength: 254 nm
  Elution Mode: Isocratic
  Mobile Phase: 78:22 MPA:MPB
  Run Time: About 15 minutes Control Samples of 2-HML, 4-HML and Loratadine were prepared. Typical Peak Retention times are given in Table II.

TABLE II

| Compound Name | Description | Typical Retention Time | Relative Retention Time |
|---|---|---|---|
| 4-HML | Potential Degradation Product | 3.2 | 0.48 |
| 2-HML | Potential Degradation | 6.3 | 0.91 |

TABLE II-continued

| Compound Name | Description | Typical Retention Time | Relative Retention Time |
|---|---|---|---|
| Loratadine | Product Active | 6.9 | 1.00 |

Test samples of spill resistant loratadine suspension were monitored after zero, three and six month stability testing for impurities. Additionally, test samples of Loratadine spill resistant suspension stressed with 5 mL of hydrogen peroxide and heated at 65° C. for sixteen hours were also sampled. All test samples had no significant quantities of the impurities.

Spill Resistant Properties of Loratadine Suspension

Spill resistant properties of loratadine suspension were evaluated in duplicate based on twelve portions of a batch of loratadine suspension stored at room temperature for four days. The relationship among pH, viscosity and the inversion, tilting, shaking and spreading spill resistant tests are summarized in Table III. The formula maintained the spill resistant property of: (a) viscosity above 5000 cps in a wide pH range (5.3-8.4), (b) the composition spreads and levels in a spoon bowl within about 1-5 seconds at room temperature (c) remains in the spoon bowl for at least about 30 seconds on spoon inversion (d) remains in the spoon bowl for at least about 30 seconds on spoon vibration and (e) remains in the spoon bowl for about 1 second on spoon tilting. Table III below, demonstrates the spill resistant properties of a loratadine sample.

TABLE III

Relationship Among pH, Viscosity and Spill Resistant Properties

| | | Spill Resistant Properties | | | |
|---|---|---|---|---|---|
| PH Value | Viscosity (cp$^1$) | Inversion (Sec) | Tilting (Sec) | Shaking (Sec) | Spreading |
| 4.79 | 2470 | <1 | <1 | <1 | 1 |
| 5.31 | 5660 | 3 | 36 | 22 | 1 |
| 5.43 | 6550 | >60 | 54 | >60 | 1.5 |
| 5.81 | 8430 | >60 | >60 | >60 | 1.5 |
| 6.22 | 9750 | >60 | >60 | >60 | 2 |
| 6.59 | 10290 | >60 | >60 | >60 | 2 |
| 6.80 | 10310 | >60 | >60 | >60 | 2 |
| 7.01 | 10420 | >60 | >60 | >60 | 2 |
| 7.44 | 10260 | >60 | >60 | >60 | 2 |
| 7.78 | 8820 | 58 | >60 | >60 | 1.5 |
| 8.36 | 7370 | 40 | 58 | >60 | 1.5 |
| 9.94 | 3590 | <1 | 2 | 3 | 1 |

We claim:

1. A storage stable pharmaceutical suspension comprising about 0.088% loratadine (w/w), about 0.24% to 0.32% (w/w) Carbomer 934P, about 0.10% (w/w) Poloxamer 188, about 5.0% (w/w) propylene glycol, about 50.0% (w/w) glycerin, about 0.20% (w/w) sucralose liquid concentrate, about 5.0% (w/w) sorbitol (crystalline), about 0.018% butylparaben, about 0.30% (w/w) masking agent and water, and having a pH of between about 6.4 and about 7.3, wherein the density of the suspension is approximately equal to the density of the loratadine, and the loratadine does not exhibit crystal growth or dissolution in the suspension.

2. The storage stable pharmaceutical suspension according to claim 1, wherein the pharmaceutical suspension has a viscosity of between about 5,000 to about 20,000 cps.

3. The storage stable pharmaceutical suspension of claim 1, wherein the pharmaceutical suspension has a viscosity of between about 5,000 to about 12,000 cps.

4. The storage stable pharmaceutical suspension of claim 1, wherein the pharmaceutical suspension has a viscosity of about 10,500 cps.

5. The storage stable pharmaceutical suspension of claim 1, wherein there is no crystalline growth during a heat-cool study for three days at 45° C.

6. The storage stable pharmaceutical suspension according to claim 1, further comprising about 0.01% (w/w) sodium hydroxide.

7. A storage stable pharmaceutical suspension comprising about 0.088% loratadine (w/w), about 0.22% to about 0.28% (w/w) Carbomer 934P, about 0.10% (w/w) Poloxamer 188, about 5.0% (w/w) propylene glycol, about 50.0% (w/w) glycerin, about 0.20% (w/w) sucralose liquid concentrate, about 5.0% (w/w) sorbitol (crystalline), about 0.018% butylparaben, about 0.30% (w/w) masking agent and water, and having a pH of between about 6.4 and about 7.3, wherein the density of the suspension is approximately equal to the density of the loratadine, and the loratadine does not exhibit crystal growth or dissolution in the suspension.

8. The storage stable pharmaceutical suspension according to claim 7, wherein the pharmaceutical suspension has a viscosity of between about 5,000 to about 20,000 cps.

9. The storage stable pharmaceutical suspension of claim 7, wherein the pharmaceutical suspension has a viscosity of between about 5,000 to about 12,000 cps.

10. The storage stable pharmaceutical suspension of claim 7, wherein the pharmaceutical suspension has a viscosity of about 10,500 cps.

11. The storage stable pharmaceutical suspension of claim 7, wherein there is no crystalline growth during a heat-cool study for three days at 45° C.

12. The storage stable pharmaceutical suspension according to claim 7, further comprising about 0.01% (w/w) sodium hydroxide.

* * * * *